United States Patent [19]

Wu

[11] Patent Number: 5,087,788
[45] Date of Patent: Feb. 11, 1992

[54] PREPARATION OF HIGH PURITY VINYLINDENE OLEFIN

[75] Inventor: Feng-Jung Wu, Baton Rouge, La.

[73] Assignee: Ethyl Corporation, Richmond, Va.

[21] Appl. No.: 663,387

[22] Filed: Mar. 4, 1991

[51] Int. Cl.$^5$ .............................................. C01J 2/24
[52] U.S. Cl. ................................................... 585/512
[58] Field of Search ................. 585/511, 512, 523, 524

[56] References Cited

U.S. PATENT DOCUMENTS

| | | | |
|---|---|---|---|
| 3,300,458 | 1/1967 | Manyik et al. | 502/118 |
| 3,472,910 | 10/1969 | Favis | 585/524 X |
| 4,404,344 | 9/1983 | Sinn et al. | 502/117 X |
| 4,658,078 | 4/1987 | Slaugh et al. | 585/512 |
| 4,704,491 | 11/1987 | Tsutsui et al. | 585/512 X |
| 4,794,096 | 12/1988 | Ewen | 502/117 |
| 4,814,540 | 3/1989 | Watanabe et al. | 585/523 |

FOREIGN PATENT DOCUMENTS 0372617 6/1990 European Pat. Off. .

Primary Examiner—W. J. Shine
Assistant Examiner—D. J. McGinty
Attorney, Agent, or Firm—David M. Bunnell

[57] ABSTRACT

A process for dimerizing an alpha-olefin of the general formula $RCH=CH_2$, where R is alkyl, cycloalkyl, or cycloalkenyl with a carbon number ranging from 1 to about 30, to a vinylidene olefin comprises contacting said alpha-olefin at temperatures between about $-60°$ C. to and $280°$ C. with a catalyst comprising (a) a metallocene having the general formula (cyclopentadienyl)$_n$MY$_{4-n}$ wherein $n=2$ or 3, M is titanium, zirconium or hafnium and each Y is individually selected from hydrogen, $C_1$–$C_5$ alkyl, $C_6$–$C_{20}$ aryl, $C_2$–$C_{20}$ alkoxy, $C_2$–$C_{20}$ ester, and halogen, (b) an alkylaluminoxane other than methyl-aluminoxane, and (c) trimethyl aluminum.

9 Claims, No Drawings

PREPARATION OF HIGH PURITY VINYLINDENE OLEFIN

BACKGROUND OF THE INVENTION

This invention relates generally to the dimerization of alpha-olefins and more specifically to a process for the dimerization of alpha-olefins to vinylidene olefins using catalyst compositions containing a metallocene such as bis(cyclopentadienyl)-zirconium dichloride, an alkylaluminoxane other than methylaluminoxane such as tri-isobutylaluminoxane, and trimethyl aluminum.

Olefin dimerization using catalysts which contain methylaluminoxane (MAO) in combination with a transition metal metallocene is disclosed, for example, in U.S. Pat. No. 4,658,078. These catalysts provide high polymerization activity but the synthesis of the MAO component is difficult and expensive because of the high reactivity of trimethylaluminum with water and the relatively low yields compared to alkylaluminoxanes such as tri-isobutylaluminoxane. Although easier to prepare, such higher alkylaluminoxanes provide inferior results when used as cocatalysts with the metallocenes. I have now discovered that catalyst systems which employ a combination of higher alkylaluminoxane and trimethylaluminum in place of methylaluminoxane provide excellent yields of high purity vinylidene olefins by the dimerization of alpha-olefins. Such vinylidene olefins are useful intermediates in preparing a number of products such as specialty detergents and lubricant additives.

BRIEF SUMMARY

In accordance with this invention there is provided a process for dimerizing an alpha-olefin of the general formula $RCH=CH_2$, where R is alkyl, cycloalkyl, or cycloalkenyl with a carbon number ranging from 1 to about 30, to a vinylidene olefin by contacting said olefin at temperatures between about $-60°$ C. and about $280°$ C. with a catalyst comprising (a) a metallocene having the general formula $(cyclopentadienyl)_nMY_{4-n}$ wherein $n=2$ or $3$, M is titanium, zirconium or hafnium and each Y is individually selected from hydrogen, $C_1$–$C_5$ alkyl, $C_6$–$C_{20}$ aryl, $C_2$–$C_{20}$ alkoxy, $C_2$–$C_{20}$ ester, and halogen, (b) an alkylaluminoxane other than methylaluminoxane, and (c) trimethyl aluminum.

DETAILED DESCRIPTION

In the present process, olefins of the general formula $RCH=CH_2$, wherein R is alkyl, cycloalkyl or cycloalkenyl and contains from 1 to about 30 carbon atoms, are contacted with a metallocene/ higher alkyl aluminoxane/trimethylaluminum catalyst system to produce vinylidene olefin dimers of the following formula:

In general, R cannot be too bulky or dimerization rates are inhibited. Mixtures of alpha-olefins can be used as starting materials and result in various cross-dimerization products. Examples of starting olefins that can be utilized in the instant process are propylene, 1-butene, 1-hexene, 1-octene, 1-eicosene, 4-vinyl-1-cyclohexene and the like.

The metallocene compounds which are useful in the catalyst compositions catalyst components, are known in the art and are either commercially available or are readily prepared.

The metallocene component includes compounds of the transition metals, titanium, zirconium and hafnium, with zirconium compounds being preferred. The cyclopentadienyl moiety is derived either from unsubstituted cyclopentadiene or cyclopentadienes which have one or more $C_1$ to $C_{12}$ hydrocarbon radicals attached to the ring so long as the ring contains at least one hydrogen. Preferred are cyclopentadiene itself or lower alkyl substituted ($C_1$ to $C_4$) cyclopentadienes such as methylcyclopentadiene. Illustrative of some of the metallocene compounds which can be used are bis-(cyclopentadienyl)-zirconium dimethyl, bis-(cyclopentadienyl)-zirconium dichloride, bis-(cyclopentadienyl)-zirconium monomethylmonochloride, bis-(cyclopentadienyl)-titanium dichloride, bis-(cyclopentadienyl)-titanium difluoride, cyclopentadienyl-zirconium tri-(2-ethylhexanoate), bis-(cyclopentadienyl)-zirconium hydrogen chloride, bis-(cyclopentadienyl)hafnium dichloride and the like. The zirconium compounds are preferred and especially the halides.

The aluminoxane component is derived from alkylaluminum compounds wherein the alkyl groups have 2 to 20, and preferably 4 to 8 carbons. The latter have good hydrocarbon solvent solubility and can be readily prepared in almost quantitative yields by adding water to organic solvent solutions of commercially available trialkylaluminum compounds such as tri-isobutylaluminum or tri-n-octylaluminum. For example, isobutylaluminoxane is prepared by adding water to tri-isobutylaluminum in $H_2O/Al$ mole ratios of from about 0.94 to 1.02.

The third component of the catalyst compositions is trimethylaluminum.

The higher alkylaluminoxane-trimethylaluminum combination used in the process of the invention with the metallocene component provides a process which is even more selective than the more expensive metallocene/methylaluminoxane system for the dimerization of alpha-olefins to vinylidene olefins in that the amount of trimer by-product is reduced.

The degree of alpha-olefin ($C_3^+$) oligomerization is affected both by the carbon number of the feed olefin and the catalyst ratios. In general, good conversion and selectivity in producing dimer is obtained at aluminum to transition metal atomic ratios of from about 1:1 to about 500:1. The optimum ratio will depend upon the alpha-olefin feed, with suitable atomic ratios for propylene, for example, being about 1:1 to 100:1 (preferred 1:1 to 50:1) and for 1-decene from about 1:1 to 1:320, preferably about 1:1 to 100:1 and most preferably about 10:1 to 75:1.

The relative molar proportions of trimethyl aluminum to aluminoxane range from about 0.1 to 10 and preferably 0.5 to 1.0.

The invention is further illustrated by, but is not intended to be limited to, the following examples.

All operations involving the use of catalyst components were conducted under an inert atmosphere. Heptane and toluene were freshly distilled under nitrogen from calcium hydride and sodium benzophenone ketyl, respectively. Tri-isobutylaluminum (TIBA) and trimethylaluminum (TMA) were commercial products of Ethyl Corporation and were used as received from the plant. $Cp_2ZrCl_2$ (Strem) was recrystallized from heptane/toluene. 1-Decene (96.0% pure) was pre-treated with activated alumina and dried over molecular sieves.

PREPARATION OF ISOBUTYLALUMINOXANE (IBAO)

The reaction was carried out in a one liter, three-necked round-bottom Morton flask equipped with a mechanical stirrer, a thermometer, and a fritted water addition tube. To this flask containing a solution of TIBA (56.2 g, 0.293 mol) in n-heptane (223 g) with vigorous stirring was added distilled water (4.80 ml, $H_2O/Al$ molar ratio = 0.94) using a syringe pump over a period of 15 minutes. The temperature was maintained at about 40° C. by applying an ice bath intermittently. After water addition was complete, the solution was stirred for one additional hour and allowed to air cool slowly. Since there was little or no insoluble material formed, a quantitative yield is assumed and Al wt % is calculated to be 3.0% which agrees well with analysis. The solution was transferred and stored under inert atmosphere. The IBAO solution thus obtained remains active after up to 6 months of its preparation.

EXAMPLE 1

A catalyst composition suitable for the dimerization of 1-decene was formed in situ in a reaction vessel. Into an 100 ml Schlenk flask was charged sequentially IBAO in n-heptane prepared as described above (3.51 gram solution, 3.90 mmol Al), TMA (0.27 gram, 3.70 mmol), 1-decene (18.0 grams, 128 mmol) and solid $Cp_2ZrCl_2$ (0.32 gram, 0.11 mmol). The mixture was heated at 50° C. with stirring. As $Cp_2ZrCl_2$ gradually dissolved, the solution turned from colorless to yellow. Aliquots were withdrawn for gas chromatographic analyses (GCA) as required. After 22 hours the solution was quenched with cooled 10% HCl solution and the organic phase was vacuum distilled. GCA showed that the 1-decene weight percent conversion was 98.6%; the yield of dimers was 8.6% and the trimer was only 1.0%. $^1$H-NMR and GC-Mass showed the distilled $C_{20}$ portion to be a mixture of 98.9% vinylidene olefins and 1.1% internal olefins.

EXAMPLES 2-3

The process of Example 1 was repeated except using the catalyst proportions and reaction conditions reported in Table I along with the results of the dimerizations.

TABLE I

1-Decene Dimerizaiton

| Example | CATALYSTS (mmol) Zr | $(RAlO)_n$ | $R_3Al$ | RXN TEMP. °C. | RXN TIME HRS | RESULTS (Wt %) UNREACTED 1-DECENE | INTERNAL DECENES | $C_{11}$ | DIMERS | TRIMERS |
|---|---|---|---|---|---|---|---|---|---|---|
| 1 | .11 | 3.9 IBAO | 3.7 TMA | 50 | 2 | 51.0 | 2.8 | 1.5 | 44.4 | .6 |
|  |  |  |  |  | 6 | 7.3 | 6.5 | 2.2 | 83.0 | .9 |
|  |  |  |  |  | 11 | 3.1 | 7.1 | 2.1 | 86.8 | 1.0 |
|  |  |  |  |  | 22 | 1.4 | 7.0 | 2.0 | 88.6 | 1.0 |
| 2 | .3 | 3.9 IBAO | 3.7 TMA | 50 | 2 | 72.6 | 3.0 | .8 | 24.1 | trace |
|  |  |  |  |  | 6 | 19.3 | 8.3 | 1.7 | 70.5 | .2 |
|  |  |  |  |  | 22 | 1.5 | 12.3 | 1.9 | 84.1 | .2 |
| 3 | .025 | 5.0 IBAO | 3.0 TMA | 50 | 2 | 28.8 | 2.9 | 1.7 | 59.5 | 6.2 |
|  |  |  |  |  | 7 | 8.6 | 4.2 | 1.8 | 76.7 | 7.6 |
|  |  |  |  |  | 23 | 3.3 | 4.8 | 1.8 | 80.9 | 7.9 |
| Comparison | .002 | 6.0 IBAO | 4.0 TMA | 50 | 5 | 82.4 | 0 | trace | 11.3 | 4.5 |
|  |  |  |  |  | 22 | 42.3 | 2.7 | trace | 34.4 | 13.9 |

EXAMPLES 4-8

The process of Example 1 was repeated except using the catalyst proportions and reaction conditions reported in Table II along with the results. Also, a 1:1 by weight mixture of toluene and 1-decene (10-12 grams of each) was used in the reaction and the IBAO was prepared using a $H_2O/Al$ molar ratio of 1.02.

TABLE II

1-Decene Dimerizaiton

| Example | CATALYSTS (mmol) Zr | $(RAlO)_n$ | $R_3Al$ | RXN TEMP. °C. | RXN TIME HRS | RESULTS (Wt %) UNREACTED 1-DECENE | INTERNAL DECENES | $C_{11}$ | DIMERS | TRIMERS |
|---|---|---|---|---|---|---|---|---|---|---|
| 4 | .3 | 3.9 IBAO | 1.8 TMA | 55 40 | 2 20 | 87.3 13.5 | 1.4 10.6 | .6 2.0 | 10.9 73.7 | trace .2 |
| 5 | .3 | 3.0 IBAO | 3.0 TMA | 50 | 2 22 | 92.8 3.6 | 1.5 16.4 | .7 3.2 | 6.3 76.3 | trace .2 |
| 6 | .3 | 3.0 IBAO | 3.0 TMA | 75 | 2 6 22 | 65.3 12.5 6.5 | 5.3 16.5 18.1 | 2.1 3.5 3.4 | 27.2 67.2 71.7 | trace trace trace |
| 7 | .3 | 6.0 IBAO | 3.0 TMA | 45 | 2 6 22 | 75.8 31.3 2.1 | 3.3 8.3 14.8 | 1.0 2.2 2.5 | 19.9 58.0 80.1 | trace trace .2 |
| 8 | .3 | 6.0 IBAO | 6.0 TMA | 50 | 2 6 24 | 84.0 23.2 2.1 | 2.1 6.2 12.8 | 1.4 3.8 4.0 | 12.7 63.4 82.7 | trace .2 .2 |

EXAMPLES 9-11

The process of Example 4 was repeated except using the catalyst proportions and reaction conditions reported in Table III along with the results including the result of a comparison in which tri-isobutylaluminum (TIBA) was used instead of TMA. Also, the IBAO was prepared using a $H_2O/Al$ molar ratio of 0.94.

TABLE III

| Example | CATALYSTS (mmol) Zr | (RAlO)$_n$ | R$_3$Al | RXN TEMP. °C. | RXN TIME HRS | 1-Decene Dimerization UNREACTED 1-DECENE | RESULTS (Wt %) INTERNAL DECENES | C$_{11}$ | DIMERS | TRIMERS |
|---|---|---|---|---|---|---|---|---|---|---|
| 9 | .3 | 3.9 | .9 | 40–50 | 4 | 44.2 | 6.8 | .6 | 48.7 | trace |
|   |    | IBAO | TMA |    | 20 | 18.0 | 14.8 | .7 | 66.3 | trace |
| 10 | .3 | 3.9 | 5.4 | 50 | 2 | 27.9 | 9.1 | 3.4 | 59.5 | .2 |
|    |    | IBAO | TMA |    | 72 | 4.5 | 8.7 | 3.5 | 83.0 | .2 |
| 11 | .3 | 3.9 | 1.8 | 50 | 2 | 49.1 | 6.9 | 1.0 | 43.2 | trace |
|    |    | IBAO | TMA |    |   |      |     |     |      |       |
| Comparison | .3 | 3.9 | 1.8 | 50 | 2 | 77.1 | 8.7 | .4 | 13.6 | trace |
|    |    | IBAO | TIBA |   | 22 | 49.9 | 14.2 | .4 | 35.1 | .2 |

The comparison using TIBA gave a poor conversion of 1-decene (about 50%) after 22 hours reaction time. This amount of conversion was achieved in Example 11, using the same catalyst ratios but with TMA, in only 2 hours.

What is claimed is:

1. A process for dimerizing an alpha-olefin of the general formula RCH=CH$_2$, where R is alkyl, cycloalkyl, or cycloalkenyl with a carbon number ranging from 1 to about 30, to a vinylidene olefin, said process comprising contacting said alpha-olefin at temperature between about −60° C. and 280° C. with a catalyst comprising (a) a metallocene having the general formula (cyclopentadienyl)$_n$MY$_{4-n}$ wherein n=2 or 3, M is titanium, zirconium or hafnium and each Y is individually selected from hydrogen, C$_1$–C$_5$ alkyl, C$_6$–C$_{20}$ aryl, C$_2$–C$_{20}$ alkoxy, C$_2$–C$_{20}$ ester, and halogen, (b) an alkylaluminoxane other than methylaluminoxane, and (c) trimethyl aluminum.

2. The process of claim 1 wherein the atomic ratio of aluminum to transition metal in the catalyst from about 1:1 to 500:1.

3. The process of claim 2 wherein the atomic ratio of aluminum to transition metal in the catalyst is from about 1:1 to 100:1.

4. The process of claim 1 wherein n is 2, the transition metal is zirconium and Y is halogen.

5. The process of claim 4 wherein said metallocene is bi-(cyclopentadienyl)-zirconium dichloride.

6. The process of claim 1 wherein said aluminoxane is tri-isobutylaluminoxane.

7. The process of claim 1 wherein said metallocene is bis-(cyclopentadienyl)-zirconium dichloride and said aluminoxane is tri-isobutylaluminoxane.

8. The composition of claim 7 wherein the alpha-olefin is 1-decene, the atomic ratio of aluminum to zirconium in the composition is from about 1:1 to 320:1.

9. The composition of claim 8 wherein the atomic ratio of aluminum to zirconium in the catalyst is from about 10:1 to 75:1.

* * * * *

UNITED STATES PATENT AND TRADEMARK OFFICE
CERTIFICATE OF CORRECTION

PATENT NO. : 5,087,788
DATED : February 11, 1992
INVENTOR(S) : FENG-JUNG WU, ET AL.

It is certified that error appears in the above-identified patent and that said Letters Patent is hereby corrected as shown below:

On the title page:

[75] Inventor: reads, "Feng-Jung Wu, Baton Rouge, La."

but should read, --Feng-Jung Wu, Baton Rouge, La., and

Samuel A. Sangokoya, Baton Rouge, La.--

Column 6:

Claim 2, line 16, reads, "...catalyst from about..."

but should read, --...catalyst is from about...--.

Claim 8, line 32, reads, "... in the composition ..."
but should read, --... in the catalyst ...--.

Signed and Sealed this

Twentieth Day of July, 1993

Attest:

MICHAEL K. KIRK

Attesting Officer

Acting Commissioner of Patents and Trademarks